United States Patent
Deslandes et al.

(10) Patent No.: US 10,041,997 B2
(45) Date of Patent: Aug. 7, 2018

(54) SYSTEM AND METHOD FOR FAULT ISOLATION BY EMISSION SPECTRA ANALYSIS

(71) Applicant: FEI EFA, Inc., Fremont, CA (US)

(72) Inventors: Herve Deslandes, Sunnyvale, CA (US); Prasad Sabbineni, San Ramon, CA (US); Regina Freed, Los Altos, CA (US)

(73) Assignee: FEI EFA, Inc., Fremont, CA (US)

( * ) Notice: Subject to any disclaimer, the term of this patent is extended or adjusted under 35 U.S.C. 154(b) by 36 days.

(21) Appl. No.: 14/657,605

(22) Filed: Mar. 13, 2015

(65) Prior Publication Data

US 2015/0260789 A1 Sep. 17, 2015

Related U.S. Application Data

(60) Provisional application No. 61/952,861, filed on Mar. 13, 2014.

(51) Int. Cl.
*G01R 31/308* (2006.01)
*G01R 31/311* (2006.01)
(Continued)

(52) U.S. Cl.
CPC ....... *G01R 31/311* (2013.01); *G01N 21/9505* (2013.01); *G01N 21/956* (2013.01)

(58) Field of Classification Search
CPC .. G01R 31/311; G01R 31/2656; G01R 31/28; G01R 31/26; G01R 31/308;
(Continued)

(56) References Cited

U.S. PATENT DOCUMENTS 3,601,492 A * 8/1971 Reichard ............ G01B 11/0675
356/504
5,208,648 A 5/1993 Batchelder et al.
(Continued)

FOREIGN PATENT DOCUMENTS

CN 101344731 B 1/2011
JP 2015-175851 A 10/2015
(Continued)

OTHER PUBLICATIONS

Black, A., et al. "Optical Sampling of GHz Charge Density Modulation in Silicon Bipolar Junction Transistors," Electronics Letters, vol. 23, No. 15, 1987, p. 783-784.
(Continued)

*Primary Examiner* — Thang Le
(74) *Attorney, Agent, or Firm* — Klarquist Sparkman, LLP

(57) ABSTRACT

An apparatus and method for optical probing of a DUT is disclosed. The system enables identifying, localizing and classifying faulty devices within the DUT. A selected area of the DUT is imaged while the DUT is receiving test signals, which may be static or dynamic, i.e., causing certain of the active devices to modulate. Light from the DUT is collected and is passed through a rotatable diffracting element prior to imaging it by a sensor and converting it into an electrical signal. The resulting image changes depending on the rotational positioning of the grating. The diffracted image is inspected to identify, localize and classify faulty devices within the DUT.

21 Claims, 4 Drawing Sheets

(51) Int. Cl.
*G01N 21/956* (2006.01)
*G01N 21/95* (2006.01)

(58) Field of Classification Search
CPC .......... G01R 31/2831; G01R 31/2648; G01R 13/04; G01R 13/38; G01R 1/071; G01R 1/08; G01N 21/956; G01N 21/9501; G01N 21/66; G01N 21/95
USPC ........ 324/754.23, 97, 762.09, 555, 752, 537
See application file for complete search history.

(56) References Cited

U.S. PATENT DOCUMENTS

| | | | |
|---|---|---|---|
| 5,220,403 A | 6/1993 | Batchelder et al. | |
| 5,289,260 A * | 2/1994 | Miyazaki | G06K 9/74 356/237.5 |
| 5,940,545 A | 8/1999 | Kash et al. | |
| 6,064,477 A * | 5/2000 | Matsumoto | G01N 21/94 356/237.2 |
| 6,081,325 A * | 6/2000 | Leslie | G01N 21/94 356/237.2 |
| 6,263,099 B1 * | 7/2001 | Maeda | G01N 21/8806 356/394 |
| 6,943,572 B2 | 9/2005 | Desplats et al. | |
| 7,012,537 B2 | 3/2006 | Woods et al. | |
| 7,038,442 B2 | 5/2006 | Desplats et al. | |
| 7,224,828 B2 | 5/2007 | Cotton et al. | |
| 7,295,301 B2 * | 11/2007 | Yu | G03F 1/84 356/237.2 |
| 7,323,862 B2 | 1/2008 | Desplats et al. | |
| 8,416,402 B2 * | 4/2013 | Shibata | G01N 21/95623 356/237.2 |
| 2002/0154303 A1 * | 10/2002 | Maeda | G01N 21/8806 356/394 |
| 2004/0146295 A1 * | 7/2004 | Furman | G01N 21/8806 398/9 |
| 2005/0168730 A1 * | 8/2005 | Sakai | G01N 21/94 356/237.4 |
| 2009/0002717 A1 * | 1/2009 | Pfaff | G01R 15/241 356/521 |
| 2009/0046288 A1 * | 2/2009 | Crafts | G01J 3/18 356/328 |
| 2011/0043775 A1 | 2/2011 | Van De Kerkhof et al. | |
| 2011/0242312 A1 * | 10/2011 | Seki | G01N 21/9505 348/125 |
| 2013/0314710 A1 * | 11/2013 | Levy | G01N 21/211 356/402 |
| 2015/0293037 A1 | 10/2015 | Deslandes et al. | |

FOREIGN PATENT DOCUMENTS

| | | |
|---|---|---|
| JP | 2015-203700 A | 11/2015 |
| TW | 200944821 A | 11/2009 |
| TW | 201538965 A | 10/2015 |

OTHER PUBLICATIONS

Bruce, M., et al. "Waveform Acquisition from the Backside of Silicon Using Electro-Optic Probing," Proceedings from the 25th International Symposium for Testing and Failure Analysis, Nov. 1999, pp. 19-25.

Heinrich, H.K., et al. "Erratum: Noninvasive Sheet Charge Density Probe for Integrated Silicon Devices," Applied Physics Letters, vol. 48, Issue 26, Jun. 1986, p. 1811.

Heinrich, H.K., et al. "Measurement of Real-Time Digital Signals in a Silicon Bipolar Junction Transistor Using a Noninvasive Optical Probe," IEEE Electronics Letters, vol. 22, No. 12, Jun. 1986, pp. 650-652.

Heinrich, H.K., et al. "Noninvasive Sheet Charge Density Probe for Integrated Silicon Devices," Applied Physics Letters, vol. 48, Issue 16, Apr. 1986, p. 1066-1068.

Heinrich, H.K., "Picosecond Noninvasive Optical Detection of Internal Electrical Signals in Flip-Chip-Mounted Silicon Integrated Circuits," IBM Journal of Research and Development, vol. 34, Issue 2/3, 1990, p. 162-172.

Hemenway, B.R., et al. "Optical Detection of Charge Modulation in Silicon Integrated Circuits Using a Multimode Laser-Diode Probe," IEEE Electron Device Letters, vol. 8, No. 8, Aug. 1987, pp. 344-346.

Kasapi, S., et al. "Laser Beam Backside Probing of CMOS Integrated Circuits," Microelectronics Reliability, vol. 39, 1999, pp. 957-961.

Kindereit, U., et al. "Comparison of Laser Voltage Probing and Mapping Results in Oversized and Minimum Size Devices of 120nm and 65nm Technology," Microelectronics Reliability, vol. 48, Issues 8/9, Sep. 2008, pp. 1322-1326, 19th European Symposium on Reliability of Electron Devices, Failure Physics and Analysis (ESREF 2008).

Kolachina, S., et al. "Optical Waveform Probing-Strategies for Non-Flipchip Devices and Other Applications," Conference Proceedings from the 27th International Symposium for Testing and Failure Analysis (ISFTA), Nov. 2001, pp. 51-57.

Rusu, S., et al. "Backside Infrared Probing for Static Voltage Drop and Dynamic Timing Measurements," 2001 IEEE International Solid-State Circuits Conference (ISSCC), Feb. 2001, Digest of Technical Papers, pp. 276-277.

Scholz, P., et al. "Single image spectral electroluminescence (photon emission) of GaN HEMTs," 2013 IEEE International Reliability Physics Symposium (IRPS), Apr. 2013, pp. CD.3.1-CD.3.7.

Soref, R.A., et al. "Electrooptical Effects in Silicon," IEEE Journal of Quantum Electronics, vol. QE-23, Issue 1, Jan. 1987, pp. 123-129.

Wilsher, K., et al. "Integrated Circuit Waveform Probing Using Optical Phase Shift Detection," Proceedings from the 26th International Symposium for Testing and Failure Analysis, Nov. 2000, pp. 479-485.

Yee, W.M., et al. "Laser Voltage Probe (LVP): A Novel Optical Probing Technology for Flip-Chip Packaged Microprocessors," Conference Proceedings from the 26th International Symposium for Testing and Failure Analysis (ISFTA), Nov. 2000, pp. 3-8.

Notice of Allowance for Taiwanese Patent Application No. 104111375 dated Jun. 13, 2016.

* cited by examiner

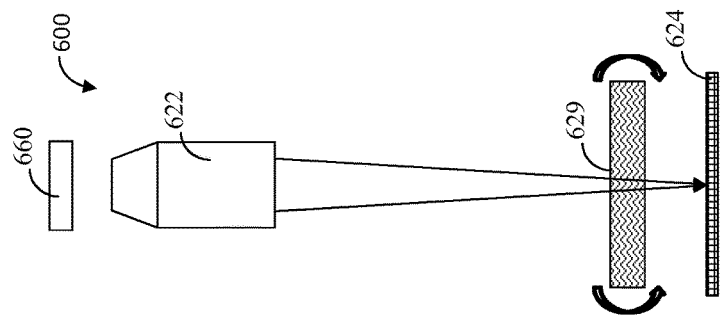
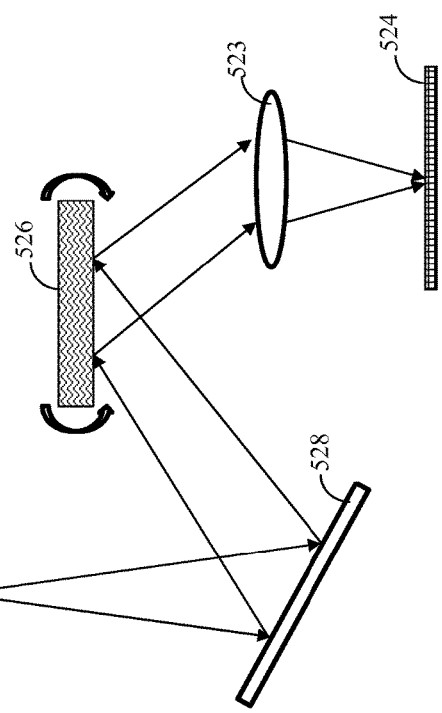
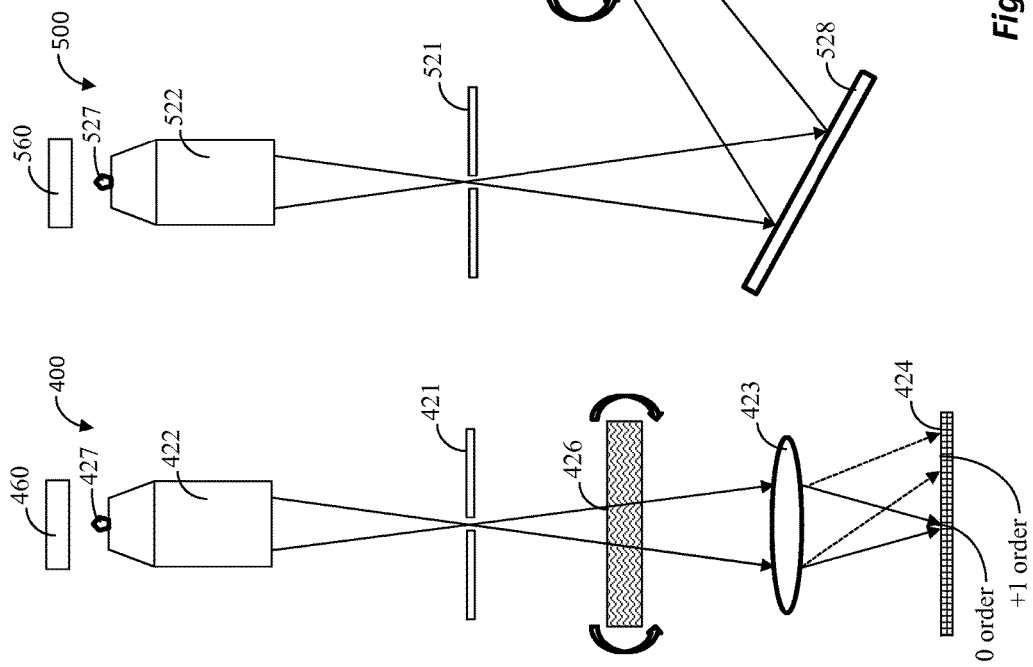

SYSTEM AND METHOD FOR FAULT ISOLATION BY EMISSION SPECTRA ANALYSIS

CROSS-REFERENCE TO RELATED APPLICATION

This application is related to and claims priority from U.S. Provisional Application Ser. No. 61/952,861, filed on Mar. 13, 2014, the disclosure of which is hereby incorporated herein by reference in its entirety.

BACKGROUND

1. Field

The present invention relates to an apparatus and method for optically probing integrated circuits by switching of an electronic elements in the device under test (DUT). The invention relates to identifying, localizing, and classifying malfunctioning elements.

2. Related Art

Probing systems have been used in the art for testing and debugging integrated circuit (IC) designs and layouts. Various emission and laser-based systems for probing IC's are known in the prior art. While some description of the prior art is provided herein, the reader is encouraged to also review U.S. Pat. Nos. 5,208,648, 5,220,403, 5,940,545, 6,943,572, 7,012,537, 7,038,442, 7,224,828, and 7,323,862, which are incorporated herein by reference in their entirety. Additional related information can be found in Yee, W. M., et al. *Laser Voltage Probe (LVP): A Novel Optical Probing Technology for Flip-Chip Packaged Microprocessors*, in International Symposium for Testing and Failure Analysis (ISTFA), 2000, p 3-8; Bruce, M. et al. *Waveform Acquisition from the Backside of Silicon Using Electro-Optic Probing*, in International Symposium for Testing and Failure Analysis (ISTFA), 1999, p 19-25; Kolachina, S. et al. *Optical Waveform Probing—Strategies for Non-Flipchip Devices and Other Applications*, in International Symposium for Testing and Failure Analysis (ISTFA), 2001, p 51-57; Soref, R. A. and B. R. Bennett, *Electrooptical Effects in Silicon*. IEEE Journal of Quantum Electronics, 1987. QE-23(1): p. 123-9; Kasapi, S., et al., Laser Beam Backside Probing of CMOS Integrated Circuits. Microelectronics Reliability, 1999. 39: p. 957; Wilsher, K., et al. Integrated Circuit Waveform Probing Using Optical Phase Shift Detection, in International Symposium for Testing and Failure Analysis (ISTFA), 2000, p 479-85; Heinrich, H. K., Picosecond Noninvasive Optical Detection of Internal Electrical Signals in Flip-Chip-Mounted Silicon Integrated Circuits. IBM Journal of Research and Development, 1990. 34(2/3): p. 162-72; Heinrich, H. K., D. M. Bloom, and B. R. Hemenway, Noninvasive sheet charge density probe for integrated silicon devices. Applied Physics Letters, 1986. 48(16): p. 1066-1068; Heinrich, H. K., D. M. Bloom, and B. R. Hemenway, Erratum to Noninvasive sheet charge density probe for integrated silicon devices. Applied Physics Letters, 1986. 48(26): p. 1811; Heinrich, H. K., et al., Measurement of real-time digital signals in a silicon bipolar junction transistor using a noninvasive optical probe. IEEE Electron Device Letters, 1986. 22(12): p. 650-652; Hemenway, B. R., et al., Optical detection of charge modulation in silicon integrated circuits using a multimode laser-diode probe. IEEE Electron Device Letters, 1987. 8(8): p. 344-346; A. Black, C. Courville, G Schultheis, H. Heinrich, Optical Sampling of GHz Charge Density Modulation in SIlicon Bipolar Junction Transistors Electronics Letters, 1987, Vol. 23, No. 15, p. 783-784, which are incorporated herein by reference in their entirety and Kindereit U, Boit C, Kerst U, Kasapi S, Ispasoiu R, Ng R, Lo W, Comparison of Laser Voltage Probing and Mapping Results in Oversized and Minimum Size Devices of 120 nm and 65 nm Technology, Microelectronics Reliability 48 (2008) 1322-1326, 19th European Symposium on Reliability of Electron Devices, Failure Physics and Analysis (ESREF 2008).

As is known, during debug and testing of an IC, a commercially available testing platform, such as, e.g., Automated Testing Equipment, also known as an Automated Testing and Evaluation (ATE) tester, is used to generate test patterns (also referred to as test vectors) to be applied to the IC device under test (DUT). Various systems and methods can then be used to test the response of the DUT to the test vectors. One such method is generally referred to as emission microscopy. Emission microscopy collects the photon emission generated inside an integrated circuit. Emission microscopy includes static emission microscopy, when photons are emitted when the signal applied to the DUT is static, and dynamic emission microscopy, when the signal applied to the DUT causes devices inside the DUT to be active, i.e., switch. Thus, in emission microscopy no illumination is used during the actual testing period. Conversely, other method utilize illumination for the testing, such as, e.g., laser voltage probing (LVP). When a laser-based system such as an LVP is used for probing, the DUT is illuminated by the laser and the light reflected from the DUT is collected by the probing system. As the laser beam strikes the DUT, the laser beam is modulated by the response of various elements (switching transistors) of the DUT to the test vectors. This has been ascribed to the electrical modulation of the free carrier density, and the resultant perturbation of the index of refraction and absorption coefficient of the material of the IC, most commonly silicon. Accordingly, analysis of the reflected light provides information about the operation of various devices in the DUT.

Emission microscopy system utilizes most of the elements of laser-based systems, since even in emission microscope illumination such as laser illumination is used for navigation and imaging of the DUT. Accordingly, a short description of a laser-based microscope is provided below, with the understanding that much of the description is equally applicable to emission system.

FIG. 1 is a general schematic depicting major components of an optical probing system architecture, 100, according to the prior art. In FIG. 1, dashed arrows represent optical path, while solid arrows represent electronic signal path. The optical paths represented by curved lines are generally made using fiber optic cables. Probe system 100 comprises a laser source which, in this particular example, is a dual laser source, DLS 110, an optical bench 112, and data acquisition and analysis apparatus 114. The optical bench 112 includes provisions for mounting the DUT 160.

A conventional ATE tester 140 provides stimulus signals and receives response signals 142 to/from the DUT 160 and may provide trigger and clock signals, 144, to the time-base board 155. The signal from the tester is generally transferred to the DUT via test boards, DUT board (adapter plate) and various cables and interfaces that connect all of these components. Generally, the ATE and the optical probing systems are produced and sold by different and unrelated companies. Thus, the reference to the description of embodiments of the inventive system relate only to the optical probing system and not to the ATE. That is, the ATE is not part of the optical probing system 100.

Turning back to the optical probing system 100, the time-base board 155 synchronizes the signal acquisition with the DUT stimulus and the laser pulses. Workstation 170 controls as well as receives, processes, and displays data from the signal acquisition board 150, time-base board 155, and the optical bench 112.

The various elements of probing system 100 will now be described in more detail. Since temporal resolution is of high importance in some testing of DUT's, the embodiment of FIG. 1 utilizes prior art pulsed lasers, wherein the laser pulse width determines the temporal resolution of the system. Dual laser source 110 consists of two lasers: a pulsed mode-locked laser, MLL 104, source that is used to generate 10-35 ps wide pulses, and a continuous-wave laser source, CWL 106, that can be externally gated to generate approximately 1 us wide pulses. The MLL 104 source runs at a fixed frequency, typically 100 MHz, and must be synchronized with the stimulus 142 provided to the DUT 160, via a phase-locked loop (PLL) on the time-base board 155, and the trigger and clock signals 144 provided by the ATE tester. The output of the DLS 110 is transmitted to the optical bench 112 using fiber optics cable 115. The light beam is then manipulated by beam optics 125, which directs the light beam to illuminate selected parts of the DUT 160.

The beam optics 125 consists of a Laser Scanning Microscope (LSM 130) and beam manipulation optics (BMO 135). The specific elements that are conventional to such an optics setup, such as objective lens, etc., are not shown. Generally, BMO 135 consists of optical elements necessary to manipulate the beam to the required shape, focus, polarization, etc., while the LSM 130 consists of elements necessary for scanning the beam over a specified area of the DUT. In addition to scanning the beam, the LSM 130 has vector-pointing mode to direct and "park" the laser beams to anywhere within the field-of-view of the LSM and Objective Lens. The X-Y-Z stage 120 moves the beam optics 125 relative to the stationary DUT 160. Using the stage 120 and the vector-pointing mode of the LSM 130, any point of interest on the DUT 160 may be illuminated and probed. In emission mode, the beam optics collects photons emitted from selected area of the DUT, e.g., using the parking mode of the LSM.

For probing the DUT 160, the ATE 140 sends stimulus signals 142 to the DUT, in synchronization with the trigger and clock signals provided to the phase-locked loop on the time-base board 155. The phase-lock loop controls the MLL 104 to synchronize its output pulses to the stimulus signals 142 to the DUT, or synchronizes the clock signal to the photon detection to provide time-resolved photon emission. MLL 104 emits laser pulses that illuminate a particular device of interest on the DUT that is being stimulated. The reflected or emitted light from the DUT is collected by the beam optics 125, and is transmitted to photodetector 138 via fiber optic cable 134. The emitted or reflected beam changes character (e.g., intensity) depending on the reaction of the device to the stimulus signal.

Incidentally, to monitor incident laser power, for purposes of compensating for laser power fluctuations, for example, optical bench 112 provides means to divert a portion of MLL 104 incident pulse to photodetector 136 via fiber optic cable 132.

The output signal of the photosensors 136, 138, is sent to signal acquisition board 150, which, in turn, sends the signal to the controller 170. By manipulation of the phase lock loop on the time-base board 155, controller 170 controls the precise time position of MLL 104 pulses with respect to DUT 160 stimulus signals 142. By changing this time position and monitoring the photosensors signals, the controller 170 can analyze the temporal response of the DUT to the stimulus signals 142. The temporal resolution of the analysis is dependent upon the width of the MLL 104 pulse.

It is also known in the art to perform continuous wave LVP, wherein a continuous wave laser is used to illuminate a device on the DUT and the continuously reflected light is collected. The continuously reflected light contains timing information relating to the response, i.e., switching, of the active device to various stimulus signals. The reflected light signal is continuously converted into electrical signal by a photodetector, e.g., avalanche photodiode (APD), and is amplified. The timing information is contained within the electrical signal and represents detected modulation of the device, which can then be displayed in either the time-domain using an oscilloscope or in the frequency domain using a spectrum analyzer.

Several issues complicate probing of DUT's, especially in view of shrinking dimensions following Moore's Law. Among the issues is identifying malfunctioning devices. That is, with the shrinking dimensions and lowering of operational voltage, it becomes more difficult to identify malfunctioning devices, either because the light emission is too faint or because light modulation is to small compared to background noise. Another issue is localizing the faulty device. That is, even if it is determined that a certain area of the DUT includes a faulty device, due to the density of devices it is difficult to know exactly where or which is the faulty device. A further issue is identifying the type of fault, so as to assist in the fault analysis. For example a faulty transistor may be overloaded or saturated. In this respect, one type of fault is when a transistor that continues to conduct as in an overloaded state. This can be caused by several mechanisms, one such being a low gate voltage. This phenomenon is referred to herein as "tristate".

Thus, advanced technology is needed in the art to assist in identifying, localizing and classifying faulty devices. In this respect, it should be noted that the general nomenclature used in the art is somewhat confusing. That is, an integrated circuit (IC) chip being tested is referred to in the art as device under test (DUT). The chip, of course, is made up of millions of electronic elements, such as transistors, diodes, etc. These are also referred to as devices. Thus, when needed to avoid confusion, the DUT will be referred to herein as IC, while the electronic elements as devices.

SUMMARY

The following summary is included in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

Various embodiments of the present invention provide apparatus and method for identifying faulty devices in an IC. Various embodiments of the present invention also provide apparatus and method for localizing the faulty devices in the IC. Moreover, various embodiments of the present invention provide apparatus and method for classifying faulty devices in the IC.

The concept behind the disclosed embodiments is the use of rotatable grating to identify, localize and classify faulty devices in the IC. The grating is used to break the detected light into its frequency components. This helps in identifying and classifying the defects. The subject inventors discovered that beneficial information can be obtained by imaging the IC using different rotational orientation of the grating. This effect is used to help identify, localize and classify the defects. Since the techniques and embodiments described herein are particularly beneficial in emission microscopy, both static and dynamic, much of the remainder of the description refers to emission microcopy.

In essence, while in standard emission systems the collected light appears circular, inserting a diffraction element in the light collection path causes the spectra of the emission to be imaged and appear generally in a linear form, according to the amount of diffraction. The orientation of the spectra may appear different, i.e., the axis of the spectra oriented at different angle, depending on the rotation of the diffration element. Additionally, the shape of the spectra itself may look different, e.g., as a linear streak, as a "comet tail," as a "teardrop," etc., depending on the type of fault. All these phenomena can help in identifying, localizing and classifying faulty devices. Also, when the emission appears as a streak, the distribution of frequencies along the axis of the streak can help identifying, localizing and classifying faulty devices.

An apparatus and method for probing of a DUT is disclosed. The system enables optical probing and/or imaging and mapping of defective devices within the DUT. A selected area of the DUT is probed while the DUT is receiving test signals, which, during dynamic testing, would cause certain active devices to switch. The concept works for static emission as well, i.e., the active devices do not necessarily needs to be switching. Light emitted or reflected from the DUT is collected and is converted into an electrical signal by a photosensor. The output of the photosensor is sampled and analyzed. This may be repeated for different rotational orientation of the grating that is placed in the optical path. Alternatively, data collection and analysis is performed when the best rotational orientation of the grating is achieved. In the analysis, the spectral response may be compared among different rotational orientation of the grating.

A method is disclosed comprising collecting light emitted from a selected area of an integrated circuit, passing the light through a diffracting element to obtain diffraction spectrum, projecting the diffraction spectrum on a photosensor to obtain an image of the diffraction spectrum, displaying the image of the diffraction spectrum on a monitor, and classifying a faulty device in the integrated circuit according to a shape of the image of the diffraction spectrum displayed on the monitor. The method may further include performing a profile scan over major axis of the diffraction spectrum and plotting resulting spectrum profile on the monitor, and classifying the type of fault according to the shape of the spectrum profile. The method may further include performing a plurality of profile scan all in direction perpendicular to major axis of the diffraction spectrum and comparing the resulting profile plots to detect a hot spot. In the above method, the diffracting element may be a transmissive grating and the method includes configuring the transmissive grating so as to simultaneously project both zero order and first order diffractions onto an image plane of the photosensor. The method may further include rotating the diffraction element so thereby separate multiple spectra in the image. The method may further include inserting an adjustable iris in an intermediate image plane and adjusting an opening of the adjustable iris to limit light collection to a desired field of view.

A method for optical probing of devices within an integrated circuit chip is disclosed, comprising: collecting light from a selected area of the chip using an objective assembly; passing the light through a rotatable diffracting element and onto an optical sensor; generating an image from output of the optical sensor; observing emission sites and corresponding emission spectra in the image and, when it appears that emission spectra of a plurality of emission sites may be overlapping, rotating the diffracting element to thereby obtain a second image wherein the spectra do not overlap.

A system for probing electronic devices within an integrated circuit chip is disclosed, comprising: a stage for supporting the chip; an objective assembly configured to collect light from the chip; a photosensor; a rotatable diffracting element positioned between the objective assembly and the photosensor and configured to receive collected light from the objective assembly and provide diffracted light to the sensor; a display for displaying an image corresponding to light detected by the photosensor.

Other aspects and features of the invention will become apparent from the description of various embodiments described herein, and which come within the scope and spirit of the invention as claimed in the appended claims.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 4 is a schematic of elements of an optical path 400 according to another embodiment of the invention.

FIG. 5 is a schematic of elements of an optical path 500 according to yet another embodiment of the invention.

FIG. 6 is a schematic of elements of an optical path 600 according to yet another embodiment of the invention.

Figure 1:
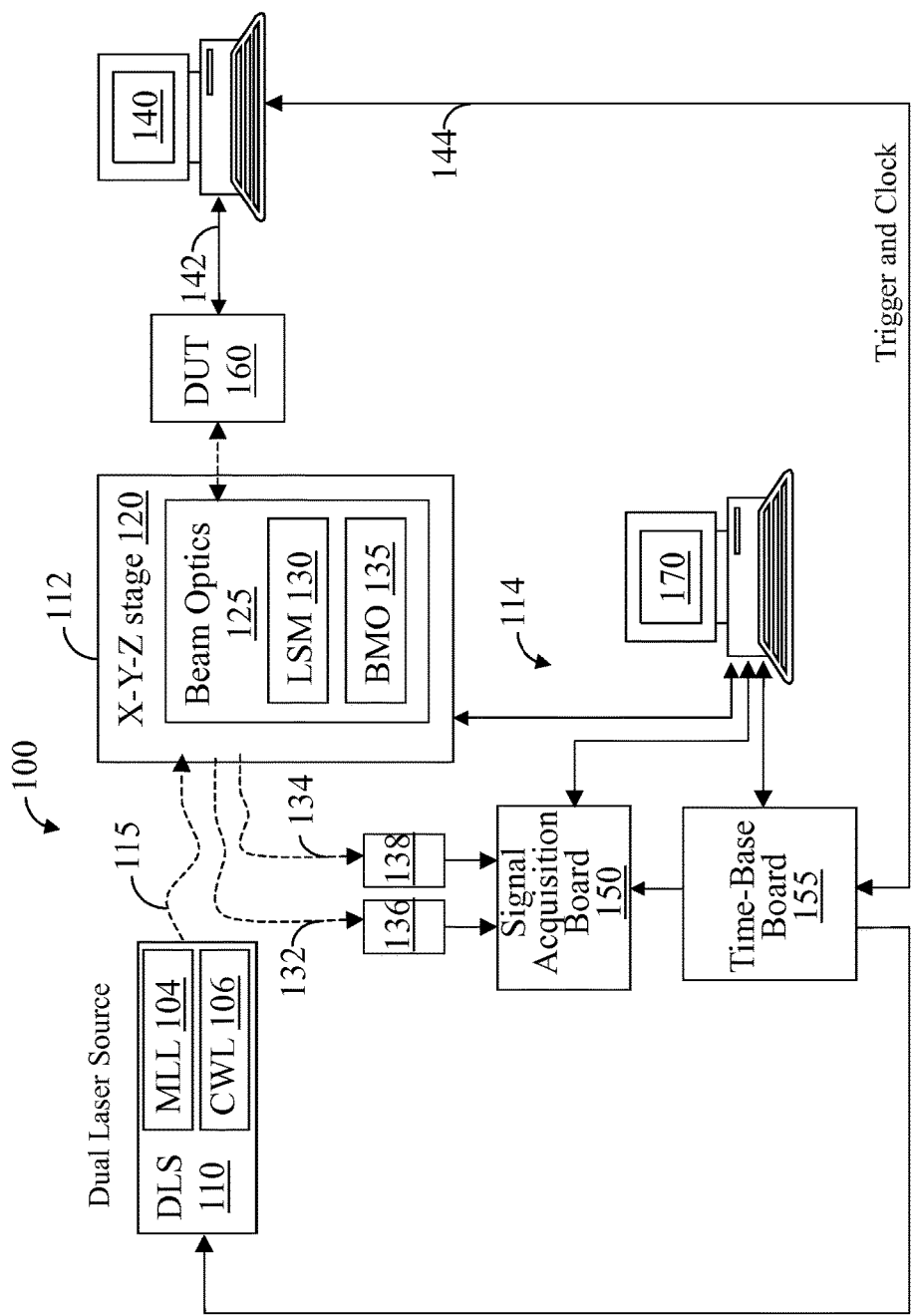
FIG. 1 is a general schematic depicting major components of a laser-based voltage probe system architecture according to the prior art.

The invention is described herein with reference to particular embodiments thereof, which are exemplified in the drawings. It should be understood, however, that the various embodiments depicted in the drawings are only exemplary and may not limit the invention as defined in the appended claims.

DETAILED DESCRIPTION

Various embodiments of the present invention provide apparatus and method for non-invasive, non-contact method for probing active transistors within a selected area of the DUT. The described methodologies augment the prior art system by enhancing the ability to identify faulty devices or identify working transistors in a wrong state because of surrounding issues like shorts, due to process/design errors, provide improved ability to localize the faulty device even in a highly dense area, and provide method for classifying the fault to assist in failure analysis. In fact embodiments of the invention also enable identifying thermal emission. For example, conductor line resistance emission can be identified, i.e., not transistor or device but just resistive metal line emitting heat. The curve or spectral profile in that case is even more exponential than the NMOS in saturation. Various embodiments showing examples of implementation of the system will now be described.

Figure 2:
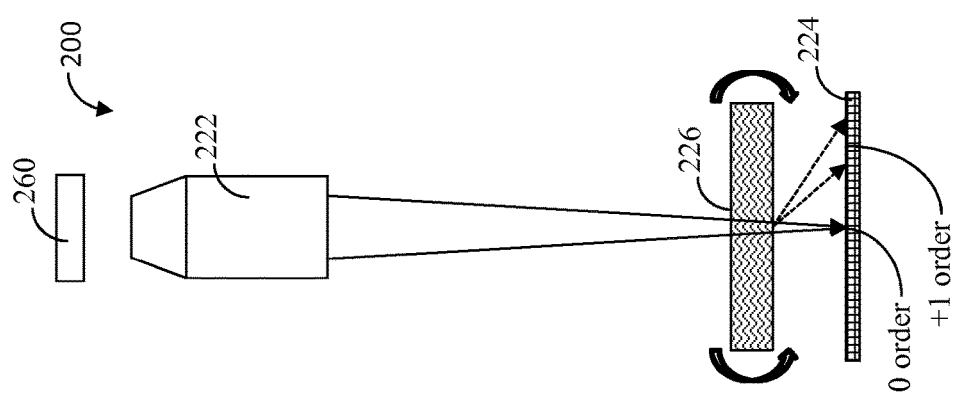
FIG. 2 is a diagram illustrating the main component of a beam manipulation optics according to an embodiment of the invention.

FIG. 2 is a schematic of elements of an optical path 200 according to an embodiment of the invention that may be implemented in any of the prior art optical system for probing DUT 260. Static and dynamic emission proper can especially benefit from this embodiment. An objective 222 collect light emitted or reflected from DUT 260. The light may traverse various optical elements that condition the light to be imaged by sensor 224. These elements are not depicted as they are known in the art and may differ from system to system. However, in the embodiment of FIG. 2, a rotatable grating 226 is inserted right ahead of the sensor 224. The sensor in this embodiment is an InGaAs camera. Other cameras, such as e.g., Short Wave Infra Red (SWIR) camera, HgCdTe camera, etc., may be used. The image of the impinging light would change depending on the rotational orientation of the grating.

It should be noted that using a diffracting element in the optical path of a prober has been suggested previously. For example, Rusu et al., suggested that by calibrating wavelength axis of spectra generated using a grating, one may be able to correlate the DC voltage difference across two points of interest. (Backside Infrared Probing for Static Voltage Drop and Dynamic Timing Measurements, S. Rusu, et al., IEEE ISSCC 2001, Session 17, TD: 3D Technology and Measurement Techniques 17.5, pp. 276, 277, 454). Similarly, Scholz et al., used a prism as a diffraction element. (Single Element Spectral Electroluminescence (Photon Emission) of GaN HEMTs, p. Scholz, et al., IEEE-IRPS 2013, pp. CD3.1-CD3.7). However, neither suggested the idea of having a rotatable diffraction element to enable identification, localization and classification of faulty devices. In fact, Scholz noted the problem of spectra overlap if more than one emitting device is within the field of view. To overcome this problem Scholz indicated that only a single emission point should be tested at a time, and all other emission sites must be no closer than the "allowable distance" provided as a function of the magnification, the dispersion ability of the prism and the spectra characteristics of the emission site. Conversely, the subject inventors have discovered that using the rotatable diffraction element one can separate the multiple emission spectra and use the rotation feature to better identify, localize and classify the faulty device. This can be further understood from the discussion of FIG. 3 below.

Figure 3:
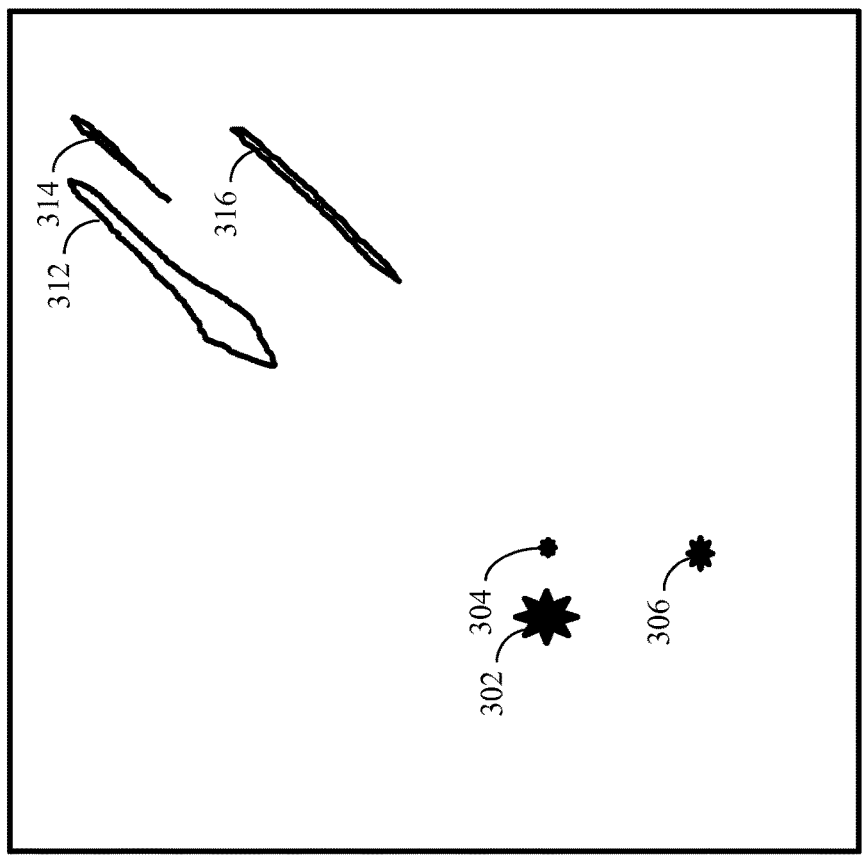
FIG. 3 is a schematic illustrating emission obtained from faulty devices using standard optics and with the addition of rotatable grating.

FIG. 3 is a schematic illustrating emission obtained from faulty devices using standard optics with the addition of rotatable grating. In FIG. 3, a transmission grating is used as the diffraction element. In this embodiment, the transmission grating is adjusted such that both the zero order and first order diffraction are simultaneously visible in the field of view. Consequently, the image of FIG. 3 shows both the emission site (zero order) and the spectra of the emission (first order) sites in the same image. The axis of each spectrum passes through the emission site. In FIGS. 3, 302, 304 and 306 are caricatures indicating the image obtained of the emission site of a diode in forward bias, an NMOS in saturation, and an NMOS in tristate, respectively. The size of the caricature conforms to the actual round emission image obtained. With the grating oriented to the maximum effect, i.e., rotated at 45°, images 312, 314 and 316, of the spectra of the diode in forward bias, the NMOS in saturation, and the NMOS in tristate, respectively, show clear separation and different character. Also, in this embodiment the grating cause the shorter wavelength to be close to the emission site, and longer wavelength further from the emission site. Thus an inspection of the shape of the spectra image or a line scan along the axis of each spectrum can help in classifying the fault.

According to one embodiment, the image is projected on a screen monitor, and the shape of the spectra image can be used to identify the type of fault. As can be seen, the NMOS in tristate provide a flat spectrum, appearing as an even streak. Conversely, the NMOS in saturation appears like a comet, i.e., tail oriented towards the emission site. The "blob" like, or "teardrop" shape (head pointing towards the emission site), spectrum of the diode can be easily distinguished from the two NMOS spectra. Thus, with a properly oriented grating, the various faulty devices can be identified, localized and classified using the spectra captured with the rotatable grating.

In FIG. 3, the grating was rotated until the best orientation was obtained to enable clear separation of the spectra and then the image captured. In FIG. 3, rotation to about 45° provided a clear separation of the spectra. Conversely, if the grating was not rotatable, the spectra from the diode and the NMOS in saturation would have overlapped, such that the spectra of these devices would not be separable. Note that the preferred rotational orientation of the grating will depend on the actual orientation of the faulty devices in the field of view. For example, in the case of FIG. 3, a 90° rotation would have caused the spectra from the two NMOS to overlap. Therefore, depending on the orientation and density of the faulty devices in the field of view, one may need to take several images with the grating oriented at different rotational angle for each image. Also, the cluster of interest may need to be separated from other clusters or the field of view reduced, which can be achieved using the embodiment illustrated in FIG. 4.

FIG. 4 is a schematic of elements of an optical path 400 according to another embodiment of the invention that may be implemented in any of the prior art optical system for probing DUT 460. An objective 422 collects light emitted or reflected from DUT 460. The light may traverse various optical elements that condition the light to be imaged by sensor 424. These elements are not depicted as they are known in the art and may differ from system to system. However, in the embodiment of FIG. 4, an adjustable iris 421 is placed in the intermediate image plane defined by the objective 422. The opening size of the iris 421 is controllable and is used to limit the field of view of the optical system 400. The iris 421 can be adjusted both in size and position. A rotatable diffraction element 426 is inserted behind the iris 421. The light from the grating 426 passes through a relay lens 423, which focuses it onto the sensor 424 (final image plane). In this embodiment as well a transmission grating 426 is used as the diffraction element and is positioned so that the zero order and first order are visible in the field of view so that they are both captured by the sensor 424 simultaneously. The image of the impinging light would change depending on the rotational orientation of the grating. Also, the movable iris 421 assists in separating the light from multiple devices, thereby enabling better localization of the faulty device. The iris size is adjusted to let one (or more) emitter light go through and its position is moved in X and Y so that it can be place on that specific emitter, hereby blocking the light of the other emitters in the field of view of the optics.

Also illustrated in FIG. 4 is a solid immersion lens (SIL) 427, which forms part of the objective assembly. The SIL may be used in any of the disclosed embodiments.

FIG. 5 is a schematic of elements of an optical path 500 according to yet another embodiment of the invention that may be implemented in any of the prior art optical system for probing DUT 560. An objective 522 with SIL 527 collect light emitted or reflected from DUT 560. The light may traverse various optical elements that condition the light to be imaged by sensor 524. These elements are not depicted as they are known in the art and may differ from system to system. However, in the embodiment of FIG. 5, a adjustable iris 521 is placed in the image plane defined by the objective 522. The opening size of the iris 521 is controllable and is used to limit the field of view of the optical system 500. A rotatable reflecting grating 526 is inserted behind the iris 521, in a light path created by the reflecting mirror 528. Mirror 528 may be a collimating mirror. The light reflected from the grating 526 passes through a relay lens 523, which focuses it onto the sensor 524. The image of the impinging light would change depending on the rotational orientation of the reflecting grating 526.

It should be appreciated that references made herein to lens encompass any optical element that acts as a lens, i.e., both transmitting and reflecting elements. Similarly, references made herein to grating encompass any element that diffracts light to its frequency components. Thus, it encompass, e.g., transmissive grating, reflective grating, prism, tunable filters, e.g., acousto-optical tunable filter, liquid crystal tunable filters, etc. The use of transmission grating has been shown to be beneficial in that it is relatively thin, so may be easily inserted in optical path of existing emission systems. Additionally, it enables simultaneously projecting both the zero order and first order diffraction images onto the image plane, such that both the emission site and its corresponding spectrum can be seen in the image. Thus, one is able to precisely identify the location of the faulty device and, from the shape of the corresponding spectra, identify and classify the type of fault.

FIG. 6 is a schematic of elements of an optical path 600 according to yet another embodiment of the invention that may be implemented in any of the prior art optical system for probing DUT 660. An objective 622 collects light emitted or reflected from DUT 660. The light may traverse various optical elements that condition the light to be imaged by sensor 624. These elements are not depicted as they are known in the art and may differ from system to system. The rotatable grating of the prior embodiments is replaced by tunable filter 629. The light from the tunable filter 629 passes onto the sensor 624. The image of the impinging light would change depending on the tuning of the tunable filter 629. The images at different tuning can help classify the fault, but may not be as efficient in localizing the fault as the rotating grating embodiments.

Figure 7:
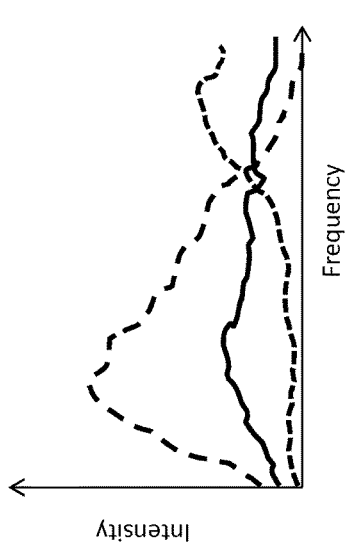
FIG. 7 illustrates a plot of arbitrary line scan along an axis of three spectra.

FIG. 7 illustrates a plot of arbitrary line scan along an axis of three spectra. The plot of solid line illustrates a rather monotonous spectrum corresponding to emission such as obtained from, e.g., an NMOS in tristate. Conversely, the plot in dashed-line shows spectrum that is weighted towards the shorter wavelengths. Such spectra is more indicative of the forward biased diode. The dotted plot illustrates a spectrum that is more pronounced at the longer wavelength, which would be indicative of an NMOS in saturation. In fact embodiments of the invention also enable identifying thermal emission. For example, conductor line resistance emission can be identified, i.e., not transistor or device but just resistive metal line emitting heat. The curve or spectral profile in that case is even more exponential than the NMOS in saturation. Thus, a line scan along the axis of each spectra can be used to classify the faults. This can be done by programming computer 170 to perform the line scanning on each obtained spectrum. Therefore, a user may be able to classify the fault by observing the shape of the image of the spectrum and by running a line scan along the axis of the spectrum.

Figure 8:
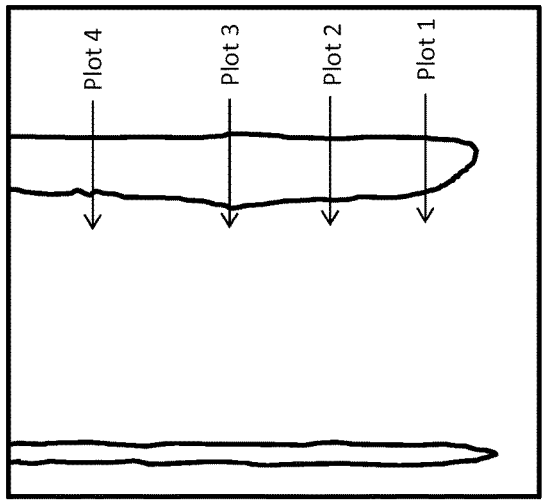
FIG. 8 illustrates an outline of the emission image (zero order) of a conductive line on the left and an outline of the spectral mapping obtained with the diffraction element on the right.
Figure 9:
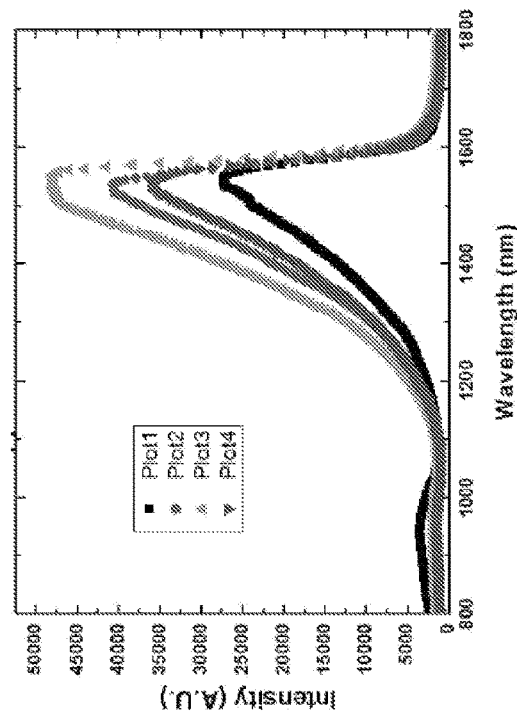
FIG. 9 illustrates profile plots along lines perpendicular to the major axis of the spectral mapping shown in FIG. 8.

As noted above, disclosed embodiment may also be used to identify simple faults, such as wire or line resistance, indicating conductor's integrity. FIG. 8 illustrates an outline of the emission image (zero order) of a conductive line on the left and an outline of the spectral mapping obtained with the diffraction element on the right. The standard emission image appears rather homogeneous, but the spectral image reveals inhomogeneity in the conductive properties of the line. That is, the higher resistance areas appear hotter than the lower resistance areas. This can be verified by plotting a spectrum profile along various points on the image, as shown in FIG. 9, wherein plot 3 appears hotter than plot 1, thus indicating that there's higher line resistance at the point where plot 3 was taken.

While the invention has been described with reference to particular embodiments thereof, it is not limited to those embodiments. Specifically, various variations and modifications may be implemented by those of ordinary skill in the art without departing from the invention's spirit and scope, as defined by the appended claims. Additionally, all of the above-cited prior art references are incorporated herein by reference.

What is claimed is:

1. A method for probing an integrated circuit, comprising:
   collecting light emitted from a selected area of the integrated circuit;
   passing the collected light through a diffracting element to break the collected light into its frequency components to obtain a diffraction spectrum;
   projecting the diffraction spectrum on a photosensor to obtain an image of the diffraction spectrum; and
   classifying a faulty device in the integrated circuit according to a shape of the image of the diffraction spectrum.

2. The method of claim 1, further comprising observing a shape of the image of the diffraction spectrum along an axis of the image of the diffraction spectrum and classifying the diffraction spectrum as corresponding to at least one potential faults.

3. The method of claim 1, further comprising inserting a controllable iris at an image plane defined by an objective assembly and adjusting the controllable iris to define the selected area.

4. The method of claim 1, further comprising obtaining a plurality of images, each at a different rotational orientation of the diffracting element and using the plurality of images to localize faulty devices.

5. The method of claim 1, further comprising performing a line scan along an axis of the image of the diffraction spectrum and generating a profile plot for the line scan.

6. The method of claim 5, wherein when the line scan is monotonous classifying a fault as a transistor that continues to conduct, while when the line scan is weighted towards the longer wavelengths classifying the fault as a transistor in saturation.

7. The method of claim 6, wherein when the line scan is weighted towards the shorter wavelengths, classifying the fault as forward biased diode.

8. The method of claim 1, further comprising applying a test signal to the integrated circuit, and wherein collecting the light from the selected area of the integrated circuit comprises collecting photon emission from the selected area of the integrated circuit.

9. The method of claim 1, wherein the diffracting element comprises a transmissive grating and the method further comprises configuring the transmissive grating so as to simultaneously project a zero order and a first order of the diffraction spectrum onto an image plane of the photosensor.

10. The method of claim 1, further comprising inserting an iris at an image plane defined by an objective assembly to define the selected area.

11. The method of claim 1, further comprising:
displaying the image of the diffraction spectrum on a monitor; and
classifying the faulty device in the integrated circuit according to the shape of the image of the diffraction spectrum displayed on the monitor.

12. A method, comprising:
collecting light emitted from a selected area of an integrated circuit;
directing the collected light to a diffracting element to obtain a diffraction spectrum;
detecting the diffraction spectrum with a photosensor; and
classifying a device in an integrated circuit according to a shape of the detected diffraction spectrum.

13. The method of claim 12, further comprising:
displaying the detected diffraction spectrum on a display; and
classifying the device according to the displayed detected diffraction spectrum.

14. The method of claim 12, wherein the detected diffraction spectrum is associated with a plurality of devices in the integrated circuit, and classifying each of the plurality of devices based on associated portions of the detected diffraction spectrum.

15. The method of claim 14, wherein at least one of the plurality of devices is classified corresponding to at least one potential fault.

16. The method of claim 12, wherein the image sensor is a camera.

17. The method of claim 12, further comprising inserting an iris at an image plane defined by an objective assembly to define the selected area.

18. The method of claim 17, wherein at least one of a size and a position of the iris is adjusted to define the selected area.

19. The method of claim 12, wherein the position of the iris is adjusted to define the selected area.

20. The method of claim 12, further comprising:
directing the collected light to the diffracting element to obtain respective diffraction spectra at a plurality of rotation angles of the diffracting element;
detecting the diffraction spectra at the plurality of rotation angles; and
classifying a plurality of devices in the integrated circuit based on the plurality of detected diffraction spectra.

21. The method of claim 12, further comprising:
directing the collected light to the diffracting element to obtain respective diffraction spectra at a plurality of rotation angles of the diffracting element;
selecting at least one of the diffractive spectra;
detecting the selected diffraction spectra; and
classifying the device in the integrated circuit based on the selected detected diffraction spectra.

* * * * *